(12) United States Patent
Blanchard et al.

(10) Patent No.: US 10,716,708 B2
(45) Date of Patent: Jul. 21, 2020

(54) PROTECTIVE EYEWEAR SYSTEMS AND METHODS

(71) Applicant: 100% SPEEDLAB, LLC, San Diego, CA (US)

(72) Inventors: Marc Blanchard, Solana Beach, CA (US); Ludovic Boinnard, San Diego, CA (US); Jerome Jacques Marie Mage, Los Angeles, CA (US)

(73) Assignee: 100% SPEEDLAB, LLC, San Diego, CA (US)

( * ) Notice: Subject to any disclaimer, the term of this patent is extended or adjusted under 35 U.S.C. 154(b) by 102 days.

(21) Appl. No.: 14/548,217

(22) Filed: Nov. 19, 2014

(65) Prior Publication Data

US 2015/0074880 A1 Mar. 19, 2015

Related U.S. Application Data

(63) Continuation-in-part of application No. 29/501,895, filed on Sep. 9, 2014, now Pat. No. Des. 727,400, and a continuation-in-part of application No. 13/750,093, filed on Jan. 25, 2013.

(60) Provisional application No. 62/048,253, filed on Sep. 9, 2014.

(51) Int. Cl.
*A61F 9/02* (2006.01)
(52) U.S. Cl.
CPC .................................. *A61F 9/028* (2013.01)
(58) Field of Classification Search
CPC .......... A61F 9/028; A61F 9/025; A61F 9/026; G02C 5/008; G02C 5/02; G02C 5/10; G02C 11/08; G02C 5/14; G02C 5/146; G02C 5/16; G02C 5/12; G02C 5/04; G02C 5/045; G02C 5/06; G02C 1/02; G02C 1/00; G02C 1/04; G02C 1/06; G02C 1/08
USPC ........................ 2/436; 351/41, 124, 125, 111
See application file for complete search history.

(56) References Cited

U.S. PATENT DOCUMENTS

| 2,387,821 | A | | 10/1945 | Berateili et al. |
| 2,846,684 | A | | 8/1958 | Hill |
| 3,368,221 | A | | 2/1968 | Anderson |
| 3,517,393 | A | | 6/1970 | Beauchef |
| 4,271,538 | A | | 6/1981 | Montesi et al. |
| 4,317,240 | A | * | 3/1982 | Angerman .............. A61F 9/025 2/436 |
| 4,425,669 | A | * | 1/1984 | Grendol .................. A61F 9/028 2/436 |
| 4,730,915 | A | * | 3/1988 | Jannard ................... A61F 9/025 351/44 |
| 4,785,481 | A | | 11/1988 | Palmer, III et al. |

(Continued)

*Primary Examiner* — Anna K Kinsaul
*Assistant Examiner* — F Griffin Hall
(74) *Attorney, Agent, or Firm* — Haynes and Boone, LLP

(57) ABSTRACT

Techniques are disclosed for systems and methods to provide an eye protection device with an extended vertical view. An eye protection device includes a frame having an outer surface that is oriented away from a user's face and an inner surface that is oriented towards the user's face. The frame includes left and right temples configured to secure the eye protection device to the user and a central raised portion disposed between a left portion and a right portion of a top portion of the frame. The central raised portion extends vertically above a substantially continuous profile of the left and right portions to provide an extended vertical view.

19 Claims, 11 Drawing Sheets

(56) References Cited

U.S. PATENT DOCUMENTS

| | | | |
|---|---|---|---|
| 4,824,233 A * | 4/1989 | Jannard | A61F 9/025 351/116 |
| 4,964,714 A | 10/1990 | Weymouth, Jr. et al. | |
| 4,977,627 A | 12/1990 | Metcalfe et al. | |
| D330,903 S * | 11/1992 | Jannard | D16/314 |
| 5,239,320 A * | 8/1993 | Allendorf | G02C 11/08 351/62 |
| 5,363,512 A | 11/1994 | Grabos, Jr. et al. | |
| D354,971 S | 1/1995 | Mugnier | |
| 5,379,464 A * | 1/1995 | Schleger | A61F 9/029 2/431 |
| D357,268 S | 4/1995 | Iida | |
| 5,444,876 A | 8/1995 | Cooper et al. | |
| 5,455,639 A * | 10/1995 | Magdelaine | A61F 9/025 2/448 |
| 5,517,700 A | 5/1996 | Hoffman | |
| 5,519,896 A * | 5/1996 | Ford | A61F 9/028 2/436 |
| D377,802 S * | 2/1997 | Leonardi | D16/313 |
| 5,610,668 A * | 3/1997 | Mage | A61F 9/028 2/435 |
| 5,898,468 A * | 4/1999 | Mage | G02C 11/08 351/41 |
| 6,029,271 A | 2/2000 | Banuchi | |
| 6,076,196 A | 6/2000 | Masumoto | |
| 6,138,285 A | 10/2000 | Robrahn et al. | |
| 6,196,676 B1 * | 3/2001 | Tabacchi | A61F 9/026 351/41 |
| 6,227,664 B1 | 5/2001 | Pavlak | |
| 6,257,719 B1 | 7/2001 | Pavlak | |
| 6,481,845 B1 | 11/2002 | Gazzara | |
| 6,513,171 B1 * | 2/2003 | Soper | A61F 9/026 2/436 |
| 6,601,240 B2 | 8/2003 | Tsubooka | |
| 6,611,966 B1 | 9/2003 | Yamamoto et al. | |
| 6,637,038 B1 | 10/2003 | Hussey | |
| 6,665,885 B2 | 12/2003 | Masumoto | |
| D533,889 S | 12/2006 | Saderholm et al. | |
| 7,181,779 B2 | 2/2007 | Hussey | |
| D542,829 S | 5/2007 | Hsu | |
| D546,868 S | 7/2007 | Teng | |
| D622,303 S | 8/2010 | Thixton | |
| 7,891,025 B2 | 2/2011 | Kobayashi et al. | |
| 8,303,109 B2 * | 11/2012 | Matera | G02C 11/08 2/435 |
| D694,312 S | 11/2013 | Mage | |
| D711,960 S * | 8/2014 | Mage | D16/312 |
| D727,398 S * | 4/2015 | Blanchard | D16/312 |
| D727,400 S * | 4/2015 | Blanchard | D16/314 |
| D756,446 S * | 5/2016 | Yoo | D16/314 |
| 2002/0023292 A1 | 2/2002 | Masumoto | |
| 2003/0035082 A1 * | 2/2003 | Olney | A61F 9/026 351/62 |
| 2005/0179856 A1 * | 8/2005 | Van Atta | A61F 9/028 351/62 |
| 2005/0183190 A1 | 8/2005 | Hussey | |
| 2008/0013036 A1 * | 1/2008 | Daems | G02C 5/00 351/41 |
| 2008/0189838 A1 * | 8/2008 | Mage | A61F 9/02 2/436 |
| 2009/0077722 A1 * | 3/2009 | Welchel | G02C 11/08 2/436 |
| 2009/0188023 A1 * | 7/2009 | Hsu | A61F 9/026 2/436 |
| 2010/0225879 A1 * | 9/2010 | Pulito | A61F 9/026 351/137 |
| 2011/0258760 A1 | 10/2011 | Renaud-goud et al. | |
| 2011/0279771 A1 * | 11/2011 | Chen | G02C 1/04 351/140 |
| 2011/0296596 A1 | 12/2011 | Chen | |
| 2012/0324638 A1 | 12/2012 | Tobia | |
| 2013/0091623 A1 | 4/2013 | Mcculloch et al. | |
| 2014/0063438 A1 * | 3/2014 | Cater | A61F 9/028 351/62 |
| 2014/0157496 A1 | 6/2014 | Ginther et al. | |
| 2014/0208489 A1 | 7/2014 | Blanchard et al. | |
| 2015/0074880 A1 | 3/2015 | Blanchard et al. | |

* cited by examiner

PROTECTIVE EYEWEAR SYSTEMS AND METHODS

CROSS-REFERENCES TO RELATED APPLICATIONS

This patent application claims the benefit of and priority to U.S. Provisional Patent Application No. 62/048,253, filed Sep. 9, 2014 and entitled "Protective Eyewear Systems and Methods," which is hereby incorporated by reference in its entirety.

This patent application is also a continuation-in-part of U.S. Design patent application Ser. No. 29/501,895, filed Sep. 9, 2014 and entitled "Sunglasses," which is hereby incorporated by reference in its entirety.

This patent application is also a continuation-in-part of U.S. patent application Ser. No. 13/750,093, filed Jan. 25, 2013 and entitled "Air Cooled Goggle," which is hereby incorporated by reference in its entirety.

TECHNICAL FIELD

One or more embodiments relate generally to protective eyewear and, more particularly, to protective eyewear that is comfortable and provides an extended vertical view.

BACKGROUND

Protective eyewear (e.g., goggles, sunglasses, and/or other eye protection devices) are used for a wide range of activities including motorcycle racing, snowboarding, skiing, BMX, road bicycling, and other activities where eye protection is critical while maintaining good visibility in a wide range of weather conditions. Conventional eyewear have developed increasingly complex frames to create improved fit and flex characteristics and to allow the eyewear to be used with a variety of different types of helmets. Conventional eyewear have also attempted to manage airflow to prevent fogging by providing smooth, laminar airflow across the back surface of the lens. However, while protective eyewear are used in a wide range of weather conditions, one drawback to the use of conventional eyewear is that they typically prevent natural air cooling. Moreover, conventional frame designs often detrimentally restrict the user's view, which can be particularly hazardous during training and sporting events. Thus, there is a need for an improved methodology for eye protection devices that provide increased viewing areas and disburse fresh air across areas where the eyewear otherwise prevents effective cooling without introducing dust or other irritants into the eyes.

SUMMARY

Techniques are disclosed for systems and methods to provide an eye protection device with an extended vertical view. An eye protection device may include a frame having an outer surface that is oriented away from a user's face and an inner surface that is oriented towards the user's face. The frame may include left and right temples configured to secure the eye protection device to the user and a central raised portion disposed between a left portion and a right portion of a top portion of the frame. The central raised portion may extend vertically above a substantially continuous profile of the left and right portions to provide an extended vertical view.

Also disclosed is an eye protection device/sports goggle comprising a lens attached to a flexible frame and configured to be positioned over the user's eyes, the flexible frame comprising an outer surface that is oriented away from the user's face and an inner surface that generally conforms to the shape of the user's face, the inner surface completely or partially covered with a flexible liner, and one or more first apertures in the outer surface connected to one or more apertures in the inner surface by one or more channels to allow airflow through the frame to the flexible liner. In various exemplary embodiments, the flexible liner is made of foam, open-cell foam, another porous material, or other material that allows air to pass through it. In various exemplary embodiments, the device includes a screen positioned near the first aperture, between the first aperture and the second aperture, or near the second aperture. In various exemplary embodiments, the device includes a filter positioned near the first aperture, between the first aperture and the second aperture, or near the second aperture.

In one embodiment, an eye protection device includes a frame having an outer surface that is oriented away from a user's face and an inner surface that is oriented towards the user's face, where the frame includes left and right temples configured to secure the eye protection device to the user, the frame includes a central raised portion disposed between a left portion and a right portion of a top portion of the frame, and the central raised portion extends vertically above a substantially continuous profile of the left and right portions.

In another embodiment, an eye protection device includes a frame having an outer surface that is oriented away from a user's face and an inner surface that is oriented towards the user's face, and a lens removeably attached to the frame and configured to be positioned over the user's eyes and/or face. The frame may include left and right temples configured to secure the eye protection device to the user and a central raised portion disposed between a left portion and a right portion of a top portion of the frame, and the central raised portion may extend vertically above a substantially continuous profile of the left and right portions.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

DETAILED DESCRIPTION

Figure 1:
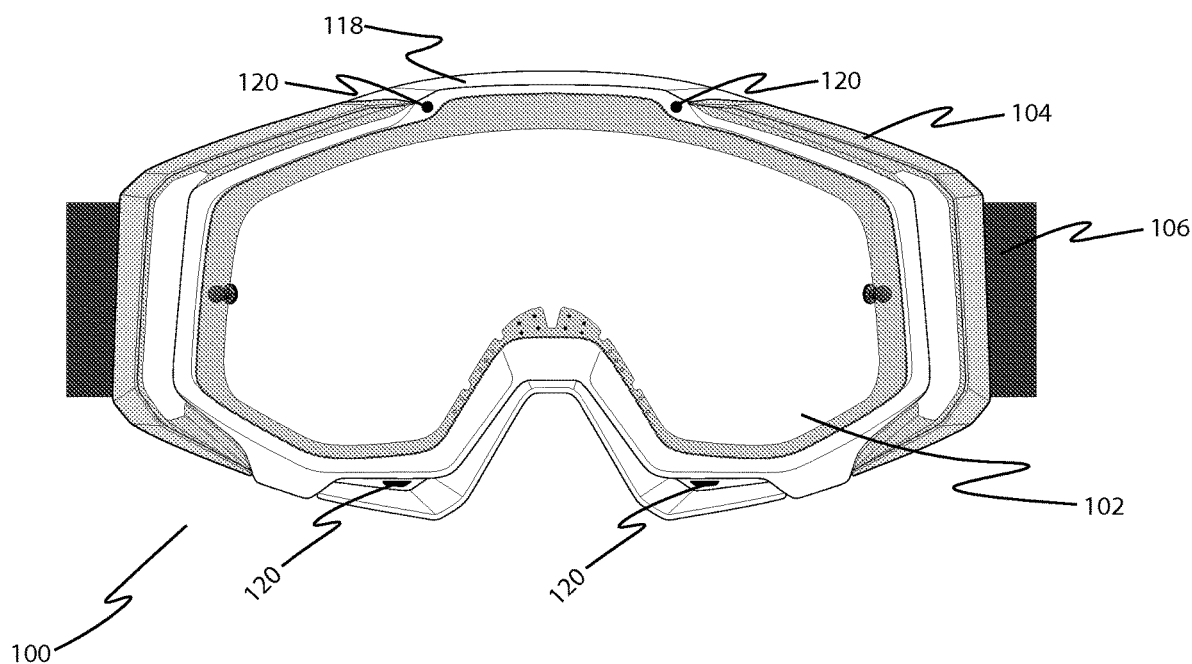
FIG. 1 is a diagram showing a front view of an embodiment of the present invention.

The following description is presented to enable any person skilled in the art to make and use the invention. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the invention. Moreover, in the present disclosure, various devices are described and set forth with regard to several embodiments. It is contemplated that features of the disclosed embodiments may be combined in any manner as may be desired for various applications and implementations. Thus, the present invention is not intended to be limited to the embodiments shown, but is to be accorded the widest possible scope consistent with the principles and features disclosed herein.

Referring to FIGS. 1 through 5, in various exemplary embodiments the invention comprises an eye protection device (e.g., goggle) 100 generally comprising a lens 102, mounted in a frame 104 and a strap 106 to hold the frame 104 and lens 102 securely against the user's face. Frame 104 is commonly made of a flexible polymer and includes an inner surface 108 that is shaped to conform to the user's face. This inner surface 108 is covered by a liner 110 such as a sheet of face foam to provide a comfortable seal against the user's face and help to absorb moisture such as perspiration.

The top area of inner surface 108 presses against the user's forehead area, the bottom area of inner surface 108 presses against the user's cheeks and across the user's nose, and the side areas of inner surface 108 press against the user's temples. Since the inner surface 108 is typically positioned behind the lens 102 and outer surface 118 of frame 104, inner surface 108 and liner 110 do not receive consistent airflow and thus may become a hot spot during exertion or in hot weather conditions that can cause discomfort and fogging issues.

Figure 2:
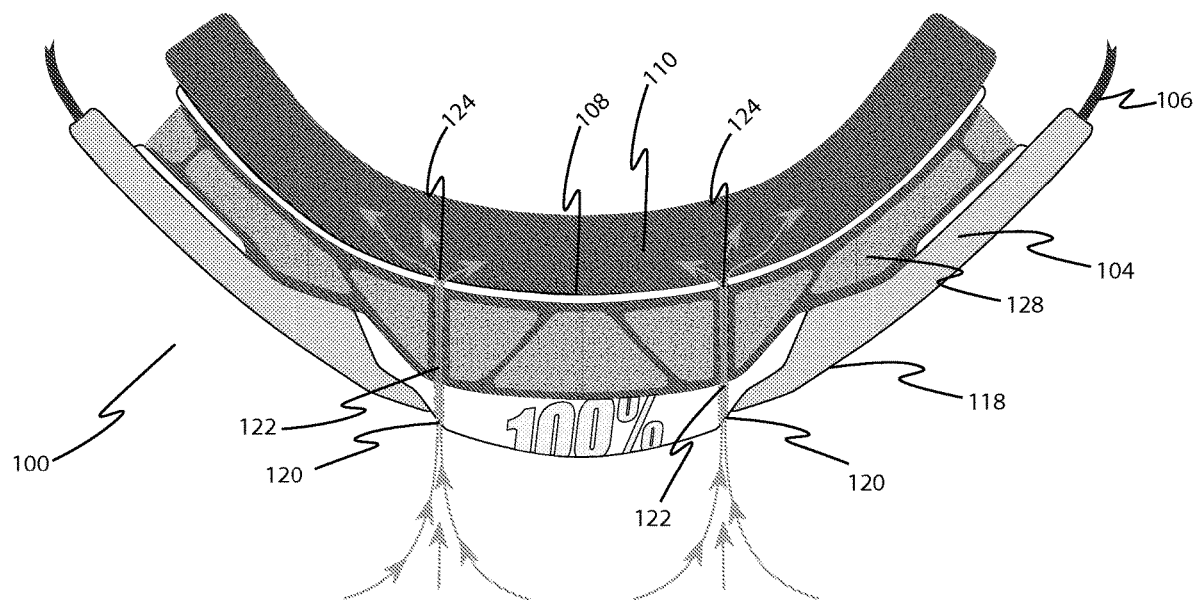
FIG. 2 is a diagram showing a top view of an embodiment of the present invention showing the air pathways through the frame of the goggle.
Figure 3:
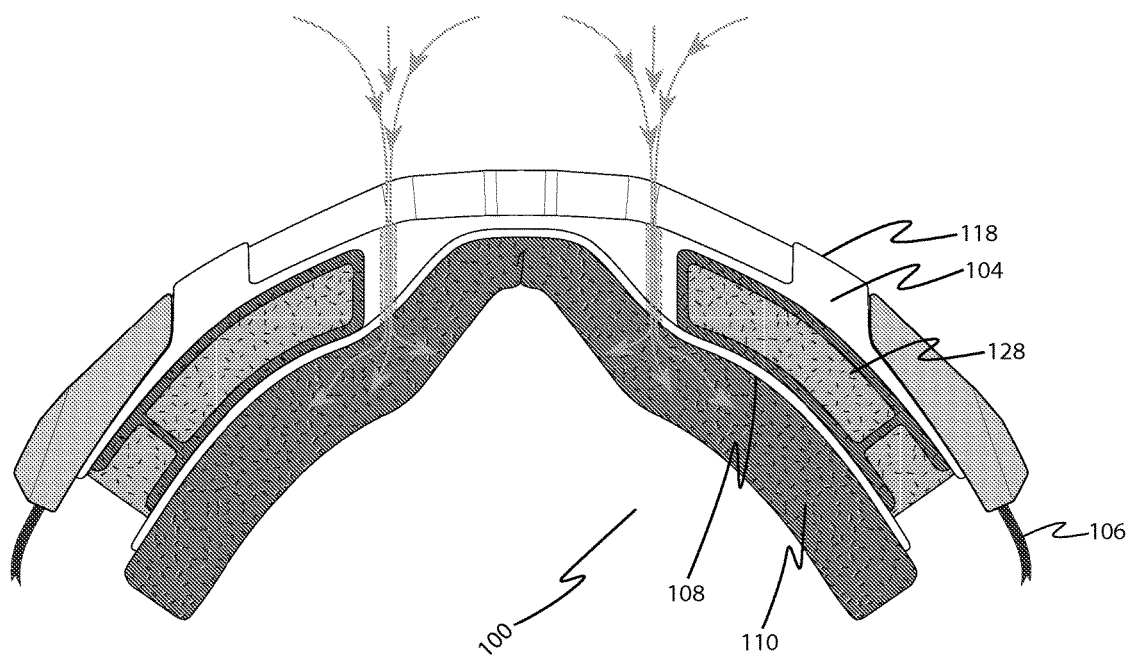
FIG. 3 is a diagram showing a bottom view of an embodiment of the present invention showing the air pathways through the frame of the goggle.
Figure 4:
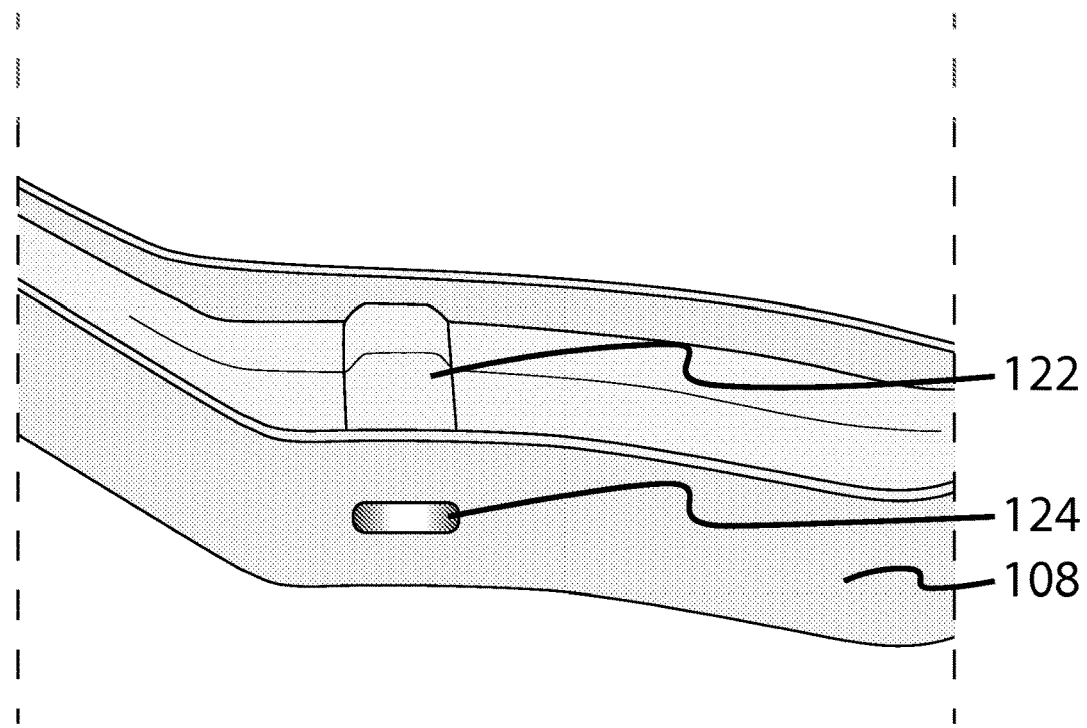
FIG. 4 is a diagram showing a section of the frame of an embodiment of the present invention.
Figure 5:
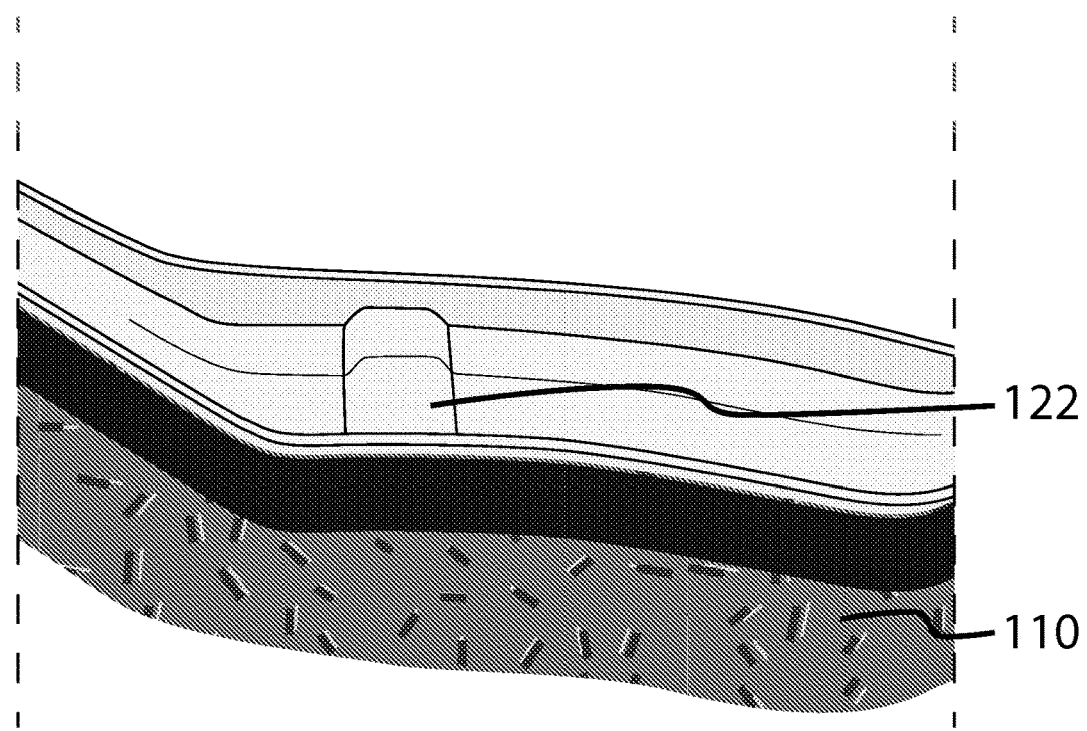
FIG. 5 is a diagram showing the same section of the frame of an embodiment of the present invention with foam positioned on the inner surface of the frame.

In an exemplary embodiment, one or more cooling vents are provided to manage airflow through the frame 104 so that it can be disbursed into the liner 110. In an exemplary embodiment, the cooling vents comprise first apertures 120 through the outer surface 118 of frame 104 that connect to channels 122 through the frame 104. These channels 122 connect to second apertures 124 through the inner surface 108. Thus, as illustrated in FIGS. 2 and 3, air flowing in through the first apertures 120 will pass along the channels 122 and through the second apertures 124, where it will be disbursed through the liner 110, cooling the liner 110 and the user's skin. Screens or other filters can be placed in the first apertures 120, channels 122, or second apertures 124 as appropriate.

Because these cooling vents provide a direct channel to the liner 110, the incoming airflow is not disbursed into the space between the lens 102 and the user's eyes and portion of their face that is within the areas circumscribed by inner surface 108. Venting into that space is typically managed by various types of direct vents 128 that allow air to flow in and out through the frame 104.

It will be readily understood that the size, shape, configuration, and orientation of the cooling vents disclosed herein can be varied while still practicing the disclosed invention. For example, goggles designed for use in dusty environments such as motocross racing may have first apertures of a relatively small size to reduce the risk of taking in large quantities of dust and dirt. Goggles designed for uses such as snowboarding or skiing may have larger apertures and channels since dust is not a concern, but may utilize some type of closure mechanism to prevent cooling when the outside air is particularly cold. The shape and contours of the channels may also be varied to manage airflow through the frame.

Referring to FIGS. 6 through 13, in various exemplary embodiments the invention comprises an eye protection device (e.g., sunglasses) 200 generally comprising a lens 202, mounted in a frame 204 and temples 206 to hold the frame 204 and lens 202 securely near and/or against a user's face. Frame 204 may be made of a rigid or flexible polymer and may include an inner surface 208 that is generally shaped to conform to the user's face. In some embodiments, portions of inner surface 208 may be covered by a liner (e.g., similar to liner 110 in FIGS. 2-3 and 5) such as a sheet of foam to provide a comfortable seal against the users face and help to absorb moisture such as perspiration. For example, such a liner may cover the inner surface of a top portion of frame 204 and press against the user's forehead area to prevent sweat from entering the space between lens 202 and the user's face. In various embodiments, inner surface 208 may include side areas 272 configured to conform generally to the shape of a user's temples. Corresponding side portions 274 of frame 202 may be configured to join temples 206 to the rest of frame 202, and/or to couple to lens 202, for example, and may be implemented as fixed, hinged, and/or curved joints and/or engagement devices, as described herein.

Figure 6:
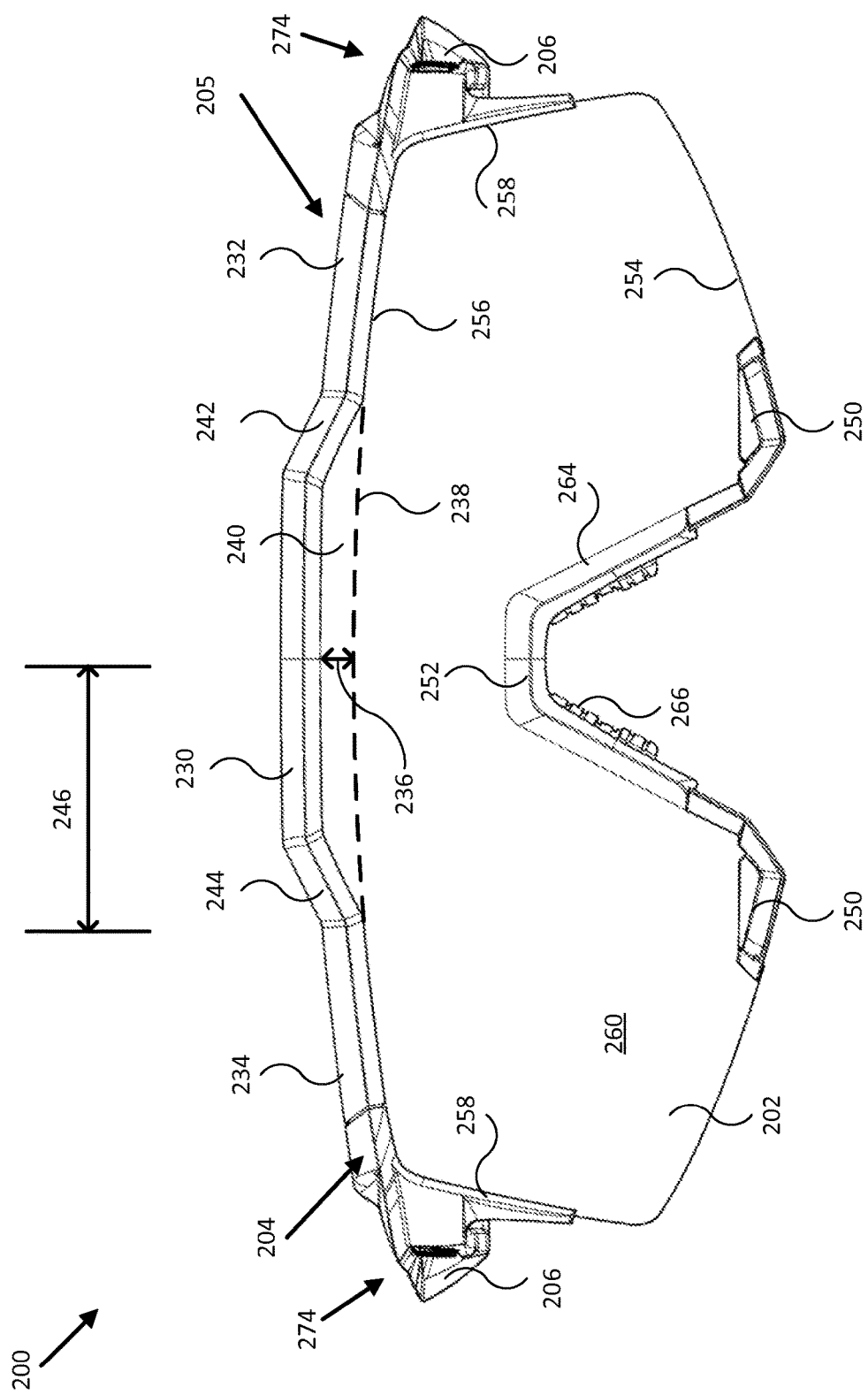
FIG. 6 is a diagram showing a front view of an embodiment of the present invention.

As shown in FIG. 6, frame 204 may in some embodiments include a central raised portion 230 disposed between left portion 232 and right portion 234 of a top portion of frame 202 (e.g., the portion of frame 204 substantially above lens 202). For example, central raised portion 230 may extend vertically a distance 236 above a substantially continuous profile (e.g., indicated by dashed line 238) corresponding to the left and right portions 232 and 234 of frame 204. In some embodiments, distance 236 may be equal to or greater than 3 mm, 3.5 mm, 4 mm, and/or other distances between 3 mm and 10 mm, for example, to allow for an extended vertical view for a user through central mesa portion 240 of lens 202. In various embodiments, central raised portion 230 may be coupled or joined to left and right portions 232 and 234 by corresponding left and right angled joints 242 and 244 formed from frame 204. In such embodiments, left and/or right angled joints 242 and/or 244 may be formed large enough to support apertures and/or channels to conduct airflow from an outer surface 205 of frame 204 to an inner surface 208 of frame 204 (e.g., see FIG. 9).

In FIG. 6, distance 246 illustrates the half width of central raised portion 230 roughly measuring the distance from the center line of central raised portion 230 (e.g., and frame 204) to a point where angled joint 244 deviates from profile 238. In some embodiments, distance 246 may be between approximately 20 mm and 60 mm, between approximately 30 mm and 60 mm, between approximately 40 mm and 60 mm, and/or other distances between approximately 20 mm and 80 mm, for example, to allow for a relatively wide extended vertical view for a user through central mesa portion 240 of lens 202. In further embodiments, distances 236 and/or 246, and/or a rake or angle of angled joints 242 and/or 244 may be adjusted to provide an increased or tailored extended vertical view for a particular eye spacing for a user, for example, yet still provide some protection from sunlight impinging upon left and/or right portions 232 and 234 of frame 204. Further, in some embodiments, frame 204 may include a relatively wide top surface 280 (e.g., see FIG. 10) to help block sunlight that would otherwise reach a user's eyes between a space between the top portion of frame 204 and a user's forehead.

Also shown in FIG. 6 are various features to provide adjustable airflow to a user wearing sunglasses 200, such as lens air scoops 250 disposed on either side of bridge 252 along a lower edge 254 of lens 202. Lens air scoops 250 may be formed from a relatively rigid or flexible polymer, for example, and/or from the same material used to form frame 204. In some embodiments, lens air scoops 250 may be glued or otherwise permanently fixed to lens 202, for example, and/or may include a hinged portion that may be used to open, close, or meter airflow through lens air scoops 250. In other embodiments, lens air scoops 250 may be removeably coupled to lens 202, for example, and/or may be formed in conjunction with corresponding apertures formed through lens 202 and displaced away from lower edge 254 of lens 202.

Lens 202 may in some embodiments be a cylindrically or otherwise cut lens approximately 2 mm thick and including various coatings, fixed appendages, and/or other structures facilitating its use as a lens for sunglasses 200. In other embodiments, lens 202 may be between 1 mm and 3 mm thick to decrease weight, for example, or increase protection against ballistic and/or other objects that would otherwise harm the user. In addition to lower edge 254, lens 202 may include top edge 256, side edges 258, outer surface 260, and inner surface 262 (e.g., see FIG. 9). Edges 254, 256, and 258 may be configured to mate with channels, notches, adhesives, and/or other engagement devices associated with frame 204, lens air scoops 250, and/or nose pad 264, for example, so as to be removable and/or interchangeable with other lenses. In some embodiments, an overall vertical provide of lens 202 may be selected from a range of profiles (e.g., height of lens 202) to reduce weight or increase airflow (e.g., with or without lens air scoops 250). As shown in FIG. 6, portions of lower edge 254 and side edges 258 may be free from any engagement device so as to reduce weight and provide for customized sizing to a user's cheek area, for example. Surfaces 260 and/or 262 may include one or more antireflective coatings, color coatings, filter coatings, hydrophobic coatings, anti-fog coatings, and/or other coatings to facilitate use of lens 202 in sunglasses 200. In some embodiments, surface 260 may support laser etching for product marketing and/or other optical features, and the material used to form lens 202 may be tinted or otherwise selected for a particular desired color. More generally, lens 202 may be made of one or more materials that are partially or totally absorptive or reflective of one or more types of ultraviolet radiation, for example, and lens 202 may be configured (e.g., through choice of materials, formation methods, polishing methods, coating application methods, and/or other configuration choices) to provide clarity of view for a user in any of a variety of different environmental conditions (e.g., desert, sea, mountain, summer, winter, and/or other environmental conditions).

Additionally shown in FIG. 6 is nose pad 264, which in some embodiments may include grip portion 266, that is configured to help secure sunglasses 200 to a user's face. For example, nose pad 264 may be configured to be positioned between bridge 252 of the eye protection device and the user's nose. Nose pad and/or grip portion may be implemented from a relatively rigid or flexible polymer or material, for example, and in some specific embodiments, grip portion 266 may be formed from and/or coated with Megol® rubber or other relatively flexible and soft material to help comfortably secure sunglasses 200 to the user's face. In some embodiments, nose pad 264 may be glued or otherwise permanently fixed to bridge 252 and/or lower edge 254 of lens 202, for example. In other embodiments, nose pad 264 may be removeably coupled to lens 202 so as to be interchangeable with other nose pads, such as nose pads designed to fit a particular user's nose or comfort level, or to provide additional protection against objects that would otherwise strike a user's face or nose.

Figure 7:
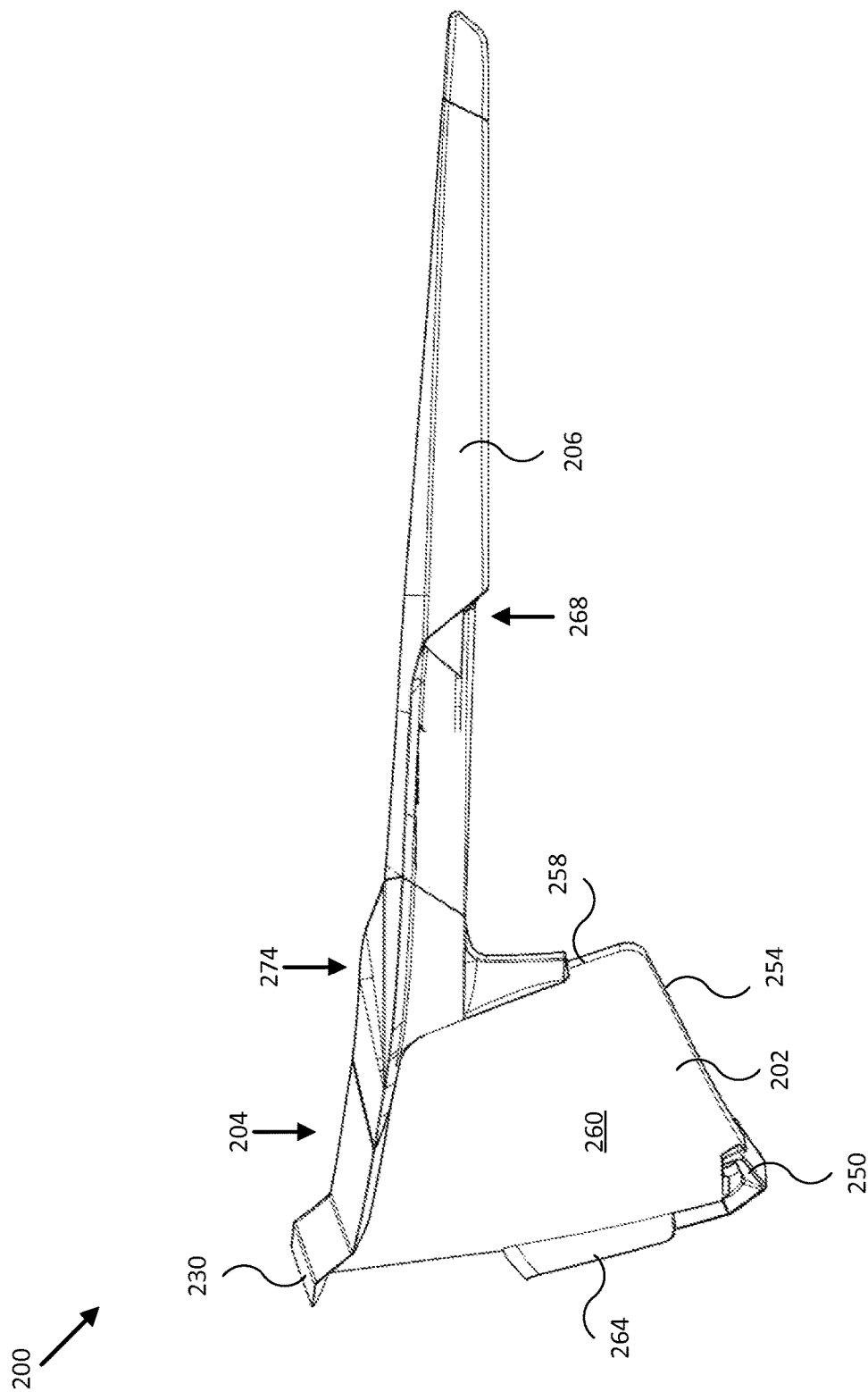
FIG. 7 is a diagram showing a side view of an embodiment of the present invention.
Figure 8:
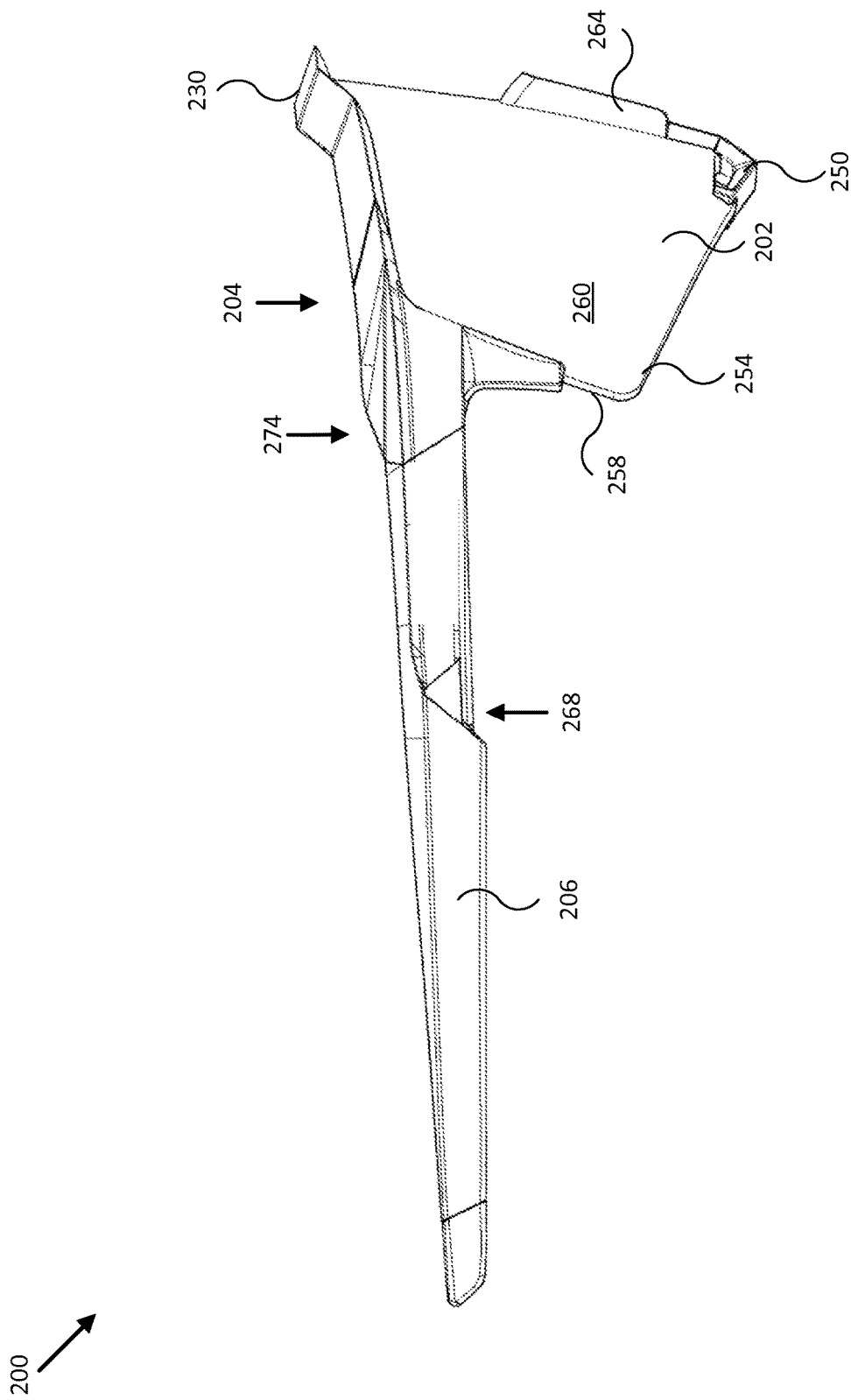
FIG. 8 is a diagram showing a side view of an embodiment of the present invention.
Figure 9:
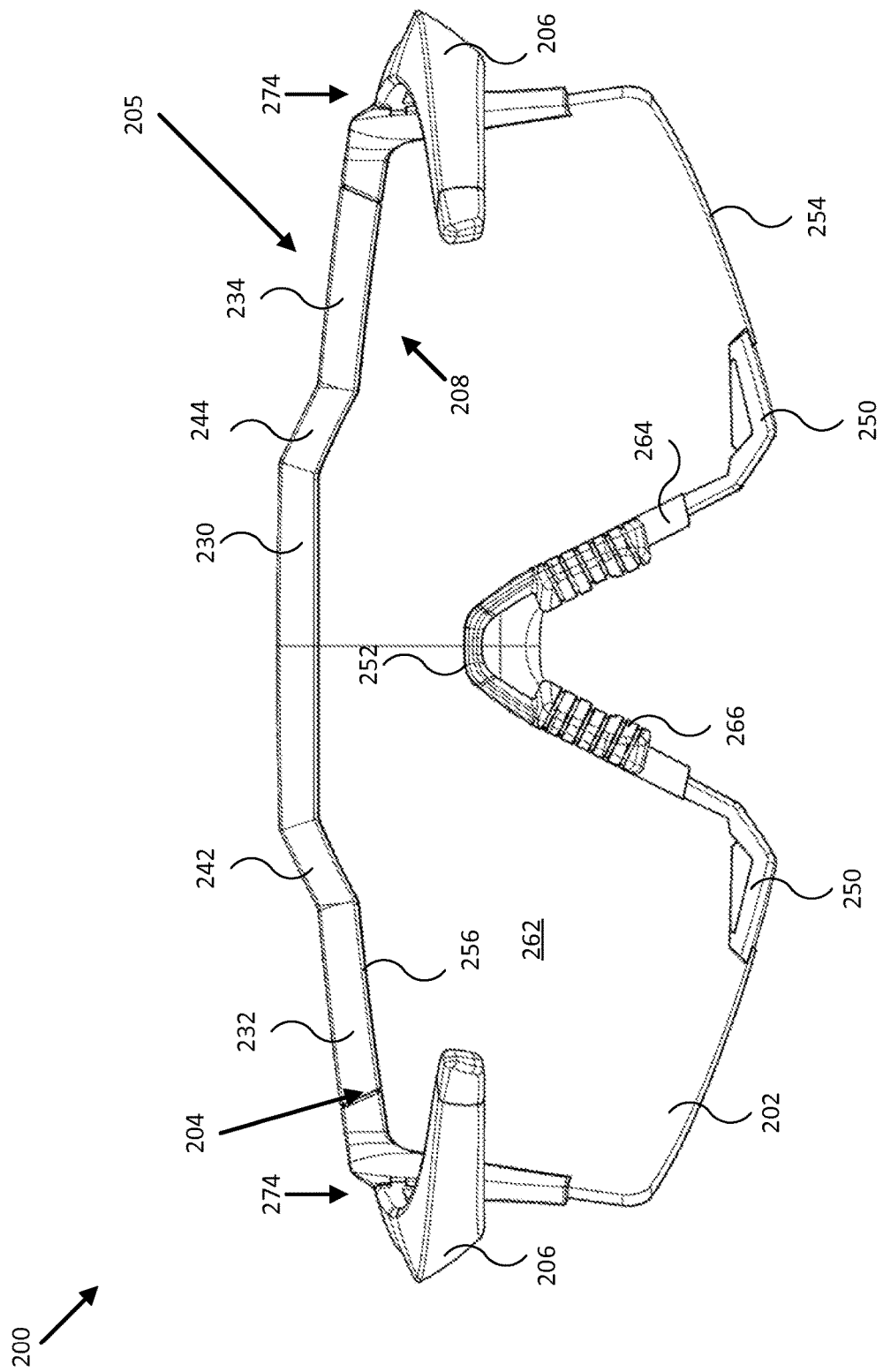
FIG. 9 is a diagram showing a rear view of an embodiment of the present invention.
Figure 10:
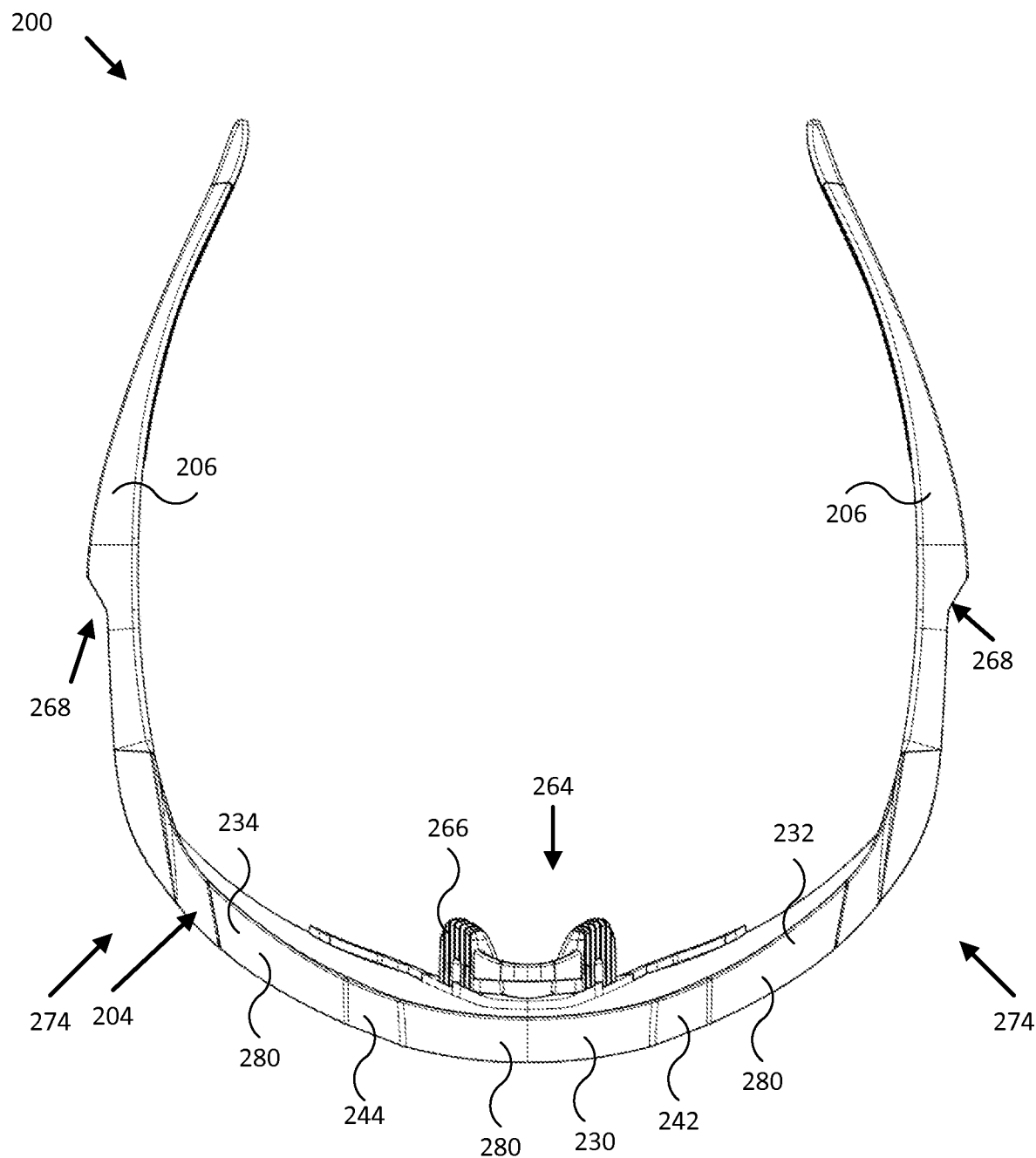
FIG. 10 is a diagram showing a top view of an embodiment of the present invention.
Figure 11:
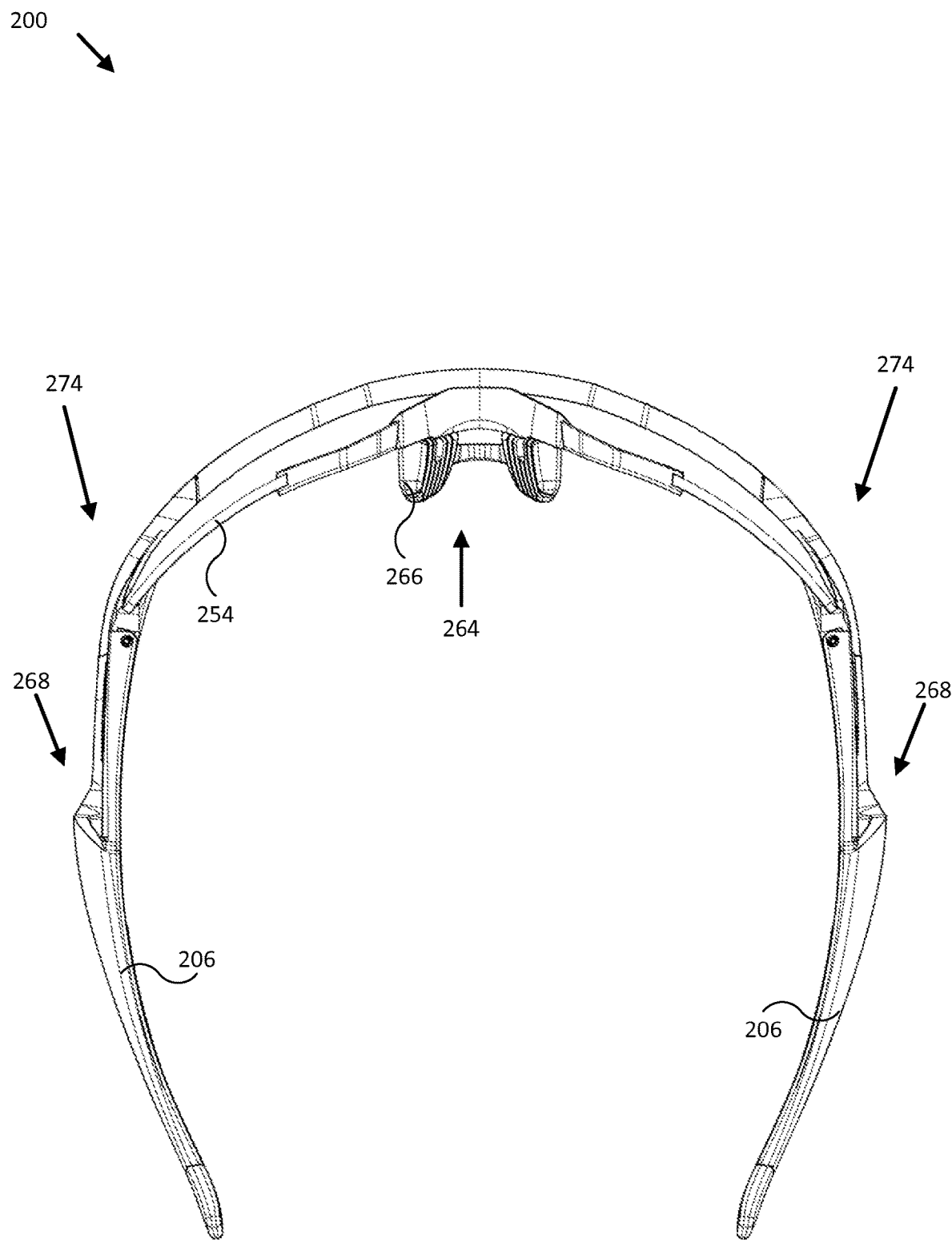
FIG. 11 is a diagram showing a bottom view of an embodiment of the present invention.

As shown in FIG. 7, in some embodiments, temples 206 of sunglasses 200 may include one or more temple air scoops 268 formed within temples 206. Temple air scoops 268 may be formed as scoop-like apertures and channels extending from an outer surface of temple 206 to an inner surface of temple 206 that is typically close to or in contact with a user's temple area. As shown, temple air scoops 268 may be configured to scoop air traveling from the front of sunglasses 200 towards the rear of sunglasses 200 generally horizontally along temple 206, for example, and deliver it to the user's temple area in order to increase airflow and decrease discomfort due to heat and/or sweat buildup between frame 204 and the user's head.

Figure 12:
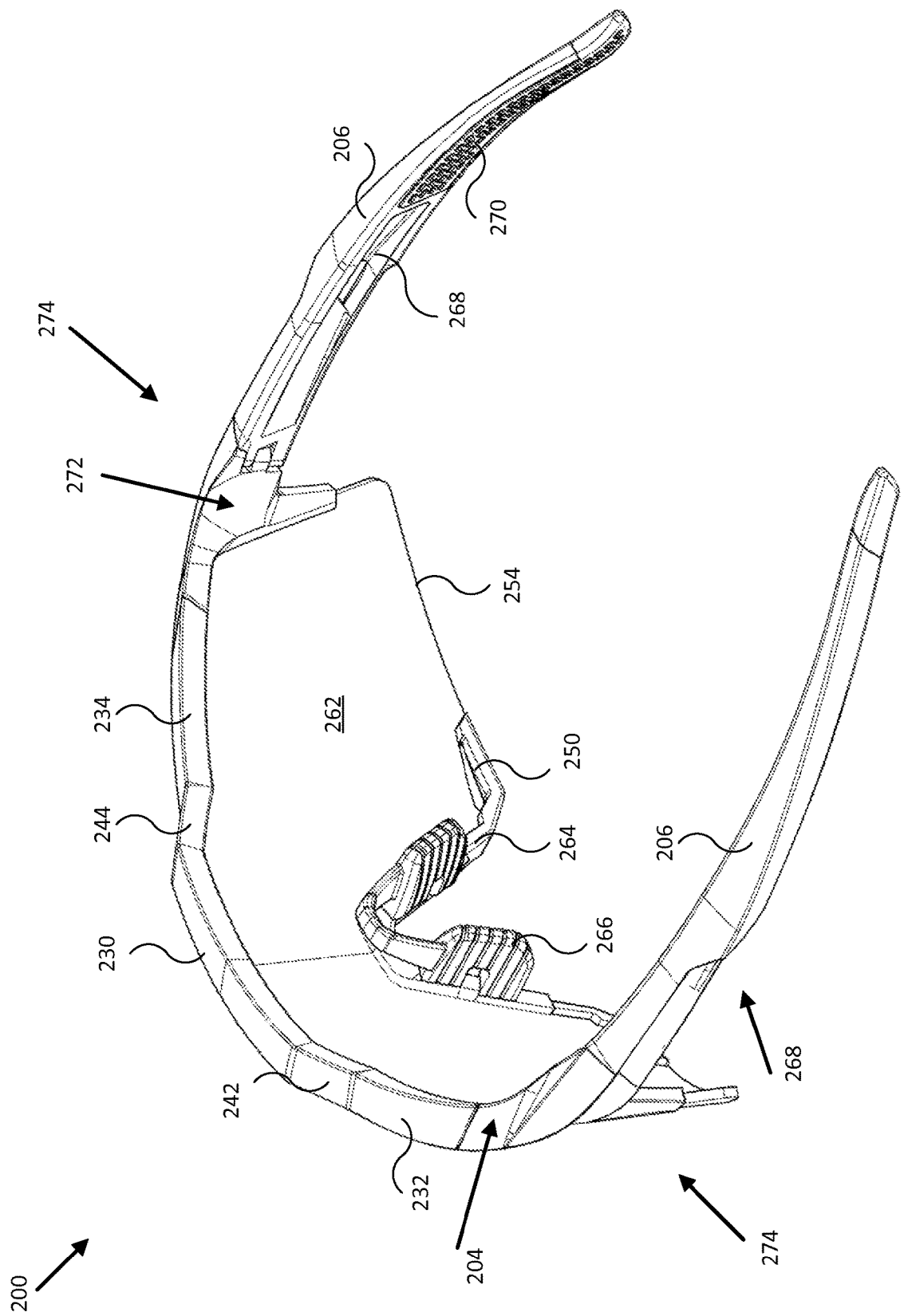
FIG. 12 is a diagram showing an orthographic view of an embodiment of the present invention.
Figure 13:
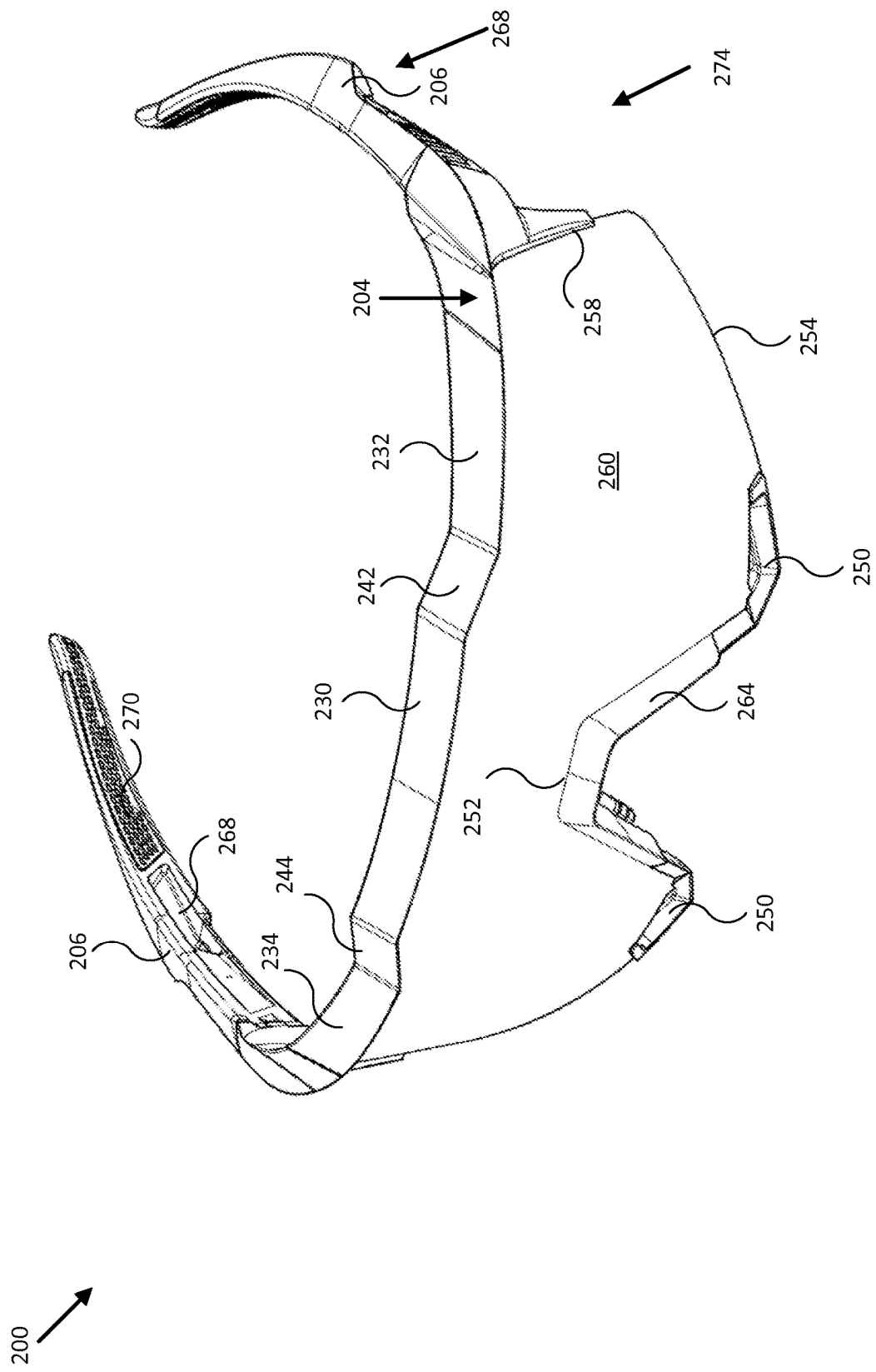
FIG. 13 is a diagram showing an orthographic view of an embodiment of the present invention.

As shown in FIGS. 12 and 13, the general wraparound design of sunglasses 200 (e.g., and/or of lens 202 and/or frame 204) facilitates securing sunglasses 200 to a user's face while providing protection from almost all angles of sunlight and/or objects that might otherwise harm a user's eyes and/or face. For example, temples 206 may include temple grip portions 270 to help comfortably secure sunglasses 200 to a user, such as without interfering with a helmet. In some embodiments, temple grip portions 270 may be formed in the same manner and/or using the same material used to form nose pad grip portions 266. Moreover, the wraparound design may be configured to provide ample space between lens 202 and a user's face, which can help increase airflow and reduce a chance of fogging/condensation. In particular, the horizontal and/or vertical curvature (e.g., or absence of curvature) of lens 202 (e.g., and/or frame 204), as shown in FIGS. 12 and 13, may provide configurable/selectable space between lens 202 and a user's face, for example, through use of the interchangeable nature of lens 202.

A typical method of use may include steps of assembly of sunglasses 200 from component parts, such as before or after testing a particular assembly for fit, adequate cooling, adequate view, and/or selecting particular components for a specific expected use, such as motocross, fishing, running, and/or other uses. For example, a first step may include inspecting frame 204 for a particular size and shape of central raised portion 230, for example, and narrowing a selection of lenses to only those that will fit frame 204. Next, a particular lens 202 may be selected according to a desired level of tint, a particular coating, a particular profile (e.g., size and/or coverage), a particular curvature, and/or other characteristics disclosed herein. Then, the selected lens may be attached to frame 204 (e.g., to top portion 205 and side portions 274 of frame 204) through use of channels and/or other engagement devices or structures of frame 204 and/or lens 202. In some embodiments, a particular lens 202 may come with attached lens air scoops 250. In other embodiments, specific lens air scoops may be selected and attached to lens 202. Next, a particular nose pad 264 may be selected for comfort, fit, and/or other desire characteristics described herein. Then, the selected nose pad 264 may be attached to lens 202 at bridge 252 and/or along lower edge 254, as shown in FIGS. 6-13. Once assembly is complete sunglasses 200 may be placed around a user's face, temple, and/or head to secure sunglasses 200 to the user. A user wearing sunglasses 200 may then participate in an activity and sunglasses 200 may provide an extended vertical view with which to see, for example, a road or vertical periphery while riding a bicycle or motorcycle and/or otherwise engaging in a sport.

Embodiments described above illustrate but do not limit the invention. It should also be understood that numerous modifications and variations are possible in accordance with the principles of the invention. Accordingly, the scope of the invention is defined only by the following claims.

What is claimed is:

1. An eye protection device comprising: a lens; a frame supporting the lens and comprising an outer surface and an inner surface, wherein the frame comprises left and right side portions with the lens disposed between the left and right side portions; a left temple coupled to the left side portion and comprising a left temple air scoop, wherein the left temple air scoop comprises a front facing first aperture disposed on an outer side of the left temple and a first channel extending from the outer side of the left temple to an inner side of the left temple, wherein the left temple comprises a front portion positioned proximate to the left side portion of the frame, and a rear portion positioned distal to the left side portion, the rear portion having a thickness between its outer and inner sides greater than the thickness of the front portion to define the front facing first aperture disposed on the outer side of the left temple; and a right temple coupled to the right side portion and comprising a right temple air scoop, wherein the right temple air scoop comprises a front facing second aperture disposed on an outer side of the right temple and a second channel extending from the outer side of the right temple to an inner side of the right temple, wherein the right temple comprises a front portion positioned proximate to the right side portion of the frame, and a rear portion positioned distal to the right side portion, the rear portion having a thickness between its outer and inner sides greater than the thickness of the front portion to define the front facing second aperture disposed on the outer side of the right temple.

2. The eye protection device of claim 1, wherein:
the frame further comprises a left portion, a right portion, a central raised portion disposed between the left portion and the right portion, a left angled joint portion connecting the left portion to the central raised portion, and a right angled joint portion connecting the right portion to the central raised portion; and
the left angled joint portion, the central raised portion, and the right angled joint portion of the frame form a mesa with the left and right angled joint portions as sides of the mesa and the central raised portion of the frame as a top side of the mesa.

3. The eye protection device of claim 1, wherein:
the frame comprises a flexible polymer; and
the inner surface comprises a top area configured to conform generally to a U shape.

4. The eye protection device of claim 2, wherein:
the central raised portion is disposed vertically above a continuous profile line formed by the left side portion, the left and right portions, and the right side portion;
each of the left and right angled joint portions extend in a straight line between the central raised portion and the left and right portions, respectively; and
the central raised portion extends in parallel to the continuous profile line and in parallel to the left and the right portions.

5. The eye protection device of claim 4, wherein the lens is fixedly or removeably attached to the frame, and wherein:
a top edge of the lens comprises a central mesa portion of the lens substantially corresponding to the mesa formed by the left angled joint portion, the right angled joint portion, and the central raised portion; and
the central mesa portion of the lens is configured to provide an extended vertical view above the continuous profile line.

6. The eye protection device of claim 5, wherein:
the lens comprises side edges corresponding to the side portions of the frame, the side edges of the lens shaped to couple to the side portions of the frame;
at least one of the frame and the lens comprises at least one of a horizontal curvature and a vertical curvature configured to provide sufficient space for at least one of increasing airflow and reducing a chance of condensation on the lens; and
the lens comprises a hydrophobic coating on at least one of an inner surface and an outer surface of the lens.

7. The eye protection device of claim 5, further comprising:
one or more lens air scoops disposed on a lower edge of the lens extending from either side of a bridge of the eye protection device, wherein the lens air scoops include angled portions configured to direct airflow around the eye protection device and are formed at least partially by the bridge, and wherein the right and left angled joints of the frame are disposed vertically over the lens air scoops.

8. The eye protection device of claim 7, further comprising a nose pad fixedly or removeably coupled to the bridge of the eye protection device, wherein the nose pad comprises a nose pad grip portion.

9. The eye protection device of claim 1, wherein:
the left temple is hingedly coupled to the left side portion of the frame to rotate relative to the frame; and
the right temple is hingedly coupled to the right side portion of the frame to rotate relative to the frame.

10. The eye protection device of claim 1, further comprising:
a flexible liner completely or partially covering at least one of a top area and side areas of the inner surface of the frame.

11. An eye protection device comprising: a frame comprising an outer surface and an inner surface; a lens removeably attached to the frame; a left temple hingedly coupled to a left side portion of the frame; and a right temple hingedly coupled to a right side portion of the frame, wherein: the left temple is configured to rotate relative to the frame and comprises a left temple air scoop including a front facing first aperture disposed on an outer side of the left temple and a first channel extending from the outer side of the left temple to an inner side of the left temple, wherein the left temple comprises a front portion positioned proximate to the left side portion of the frame, and a rear portion positioned distal to the left side portion, the rear portion having a thickness between its outer and inner sides greater than the thickness of the front portion to define the front facing first aperture disposed on the outer side of the left temple; and the right temple is configured to rotate relative to the frame and comprises a right temple air scoop including a front facing second aperture disposed on an outer side of the right temple and a second channel extending from the outer side of the right temple to an inner side of the right temple, wherein the right temple comprises a front portion positioned proximate to the right side portion of the frame, and a rear portion positioned distal to the right side portion, the rear portion having a thickness between its outer and inner sides greater than the thickness of the front portion to define the front facing second aperture disposed on the outer side of the right temple.

12. The eye protection device of claim 11, wherein:
the lens is disposed between the left side portion and the right side portion;
the frame further comprises a left portion, a right portion, a central raised portion disposed between the left portion and the right portion, a left angled joint portion connecting the left portion to the central raised portion, and a right angled joint portion connecting the right portion to the central raised portion, wherein the left angled joint portion, the central raised portion, and the right angled joint portion of the frame form a mesa with the left and right angled joint portions as sides of the mesa and the central raised portion of the frame as a top side of the mesa;
the central raised portion is disposed vertically above a continuous profile line formed by the left temple, the left and right portions, and the right temple;
the left angled joint portion is disposed at a first angle to the left portion and is disposed at a second angle to the central raised portion;
the right angled joint portion is disposed at a third angle to the right portion and is disposed at a fourth angle to the central raised portion; and
a top edge of the lens comprises portions substantially corresponding to the left portion, the left angled joint portion, the central raised portion, the right angled joint portion, and the right portion.

13. The eye protection device of claim 12, wherein:
each of the left and right angled joint portions extend in a straight line connecting the central raised portion to the left and right portions of the frame, respectively.

14. The eye protection device of claim 11, further comprising:

a nose pad fixedly or removeably coupled to the lens and configured to be positioned at a bridge of the eye protection device, wherein the nose pad comprises a nose pad grip portion; and
one or more lens air scoops formed at least partially by the bridge, wherein the lens air scoops include angled portions configured to direct airflow around the eye protection device.

15. The eye protection device of claim 12, wherein:
the lens comprises a nose bridge portion, wherein all of the bridge portion is disposed below the central raised portion, wherein the left angled joint portion is disposed more vertically than the left portion and the central raised portion, and wherein the right angled joint portion is disposed more vertically than the right portion and the central raised portion;
the top edge comprises a central mesa portion of the lens substantially corresponding to the mesa formed by the left angled joint portion, the right angled joint portion, and the central raised portion;
the central mesa portion of the lens is configured to provide an extended vertical view above the continuous profile line;
the central raised portion comprises a height greater than or equal to approximately 3 mm and a width between 40 mm and 160 mm;
the lens comprises at least one of a hydrophobic coating and an antireflective coating on at least one of an inner surface and an outer surface of the lens; and
at least one of the frame and the lens comprises at least one of a horizontal curvature and a vertical curvature configured to at least one of increase airflow and reduce a chance of condensation on the lens.

16. The eye protection device of claim 2, wherein the lens comprises a nose bridge portion, wherein the left angled joint portion is disposed distal from the left side portion, proximate to the central raised portion, and vertically proximate to the nose bridge portion, and wherein the right angled joint portion is disposed distal from the right side portion, proximate to the central raised portion, and vertically proximate to the nose bridge portion.

17. The eye protection device of claim 1, further comprising:
a nose bridge extending along a lower edge of the lens; and
one or more lens air scoops formed at least partially by or in the nose bridge.

18. The eye protection device of claim 17, wherein the one or more lens air scoops are removably coupled to the lens.

19. The eye protection device of claim 17, further comprising one or more apertures formed through the lens.

* * * * *